US008236831B2

(12) United States Patent
Kang et al.

(10) Patent No.: US 8,236,831 B2
(45) Date of Patent: Aug. 7, 2012

(54) THIAZOLE COMPOUND (AS PPARδ) LIGAND AND PHARMACEUTICAL, COSMETIC AND HEALTH FOOD COMPRISED THEREOF

(75) Inventors: Heonjoong Kang, Seongnam-si (KR); Jae-Young Ko, Seoul (KR); Hoo-Sang Hwang, Gunpo-si (KR)

(73) Assignee: Seoul National University Industry Foundation, Seoul (KR)

( * ) Notice: Subject to any disclaimer, the term of this patent is extended or adjusted under 35 U.S.C. 154(b) by 0 days.

(21) Appl. No.: 12/522,358

(22) PCT Filed: Jan. 8, 2008

(86) PCT No.: PCT/KR2008/000106
§ 371 (c)(1),
(2), (4) Date: Jul. 7, 2009

(87) PCT Pub. No.: WO2008/084962
PCT Pub. Date: Jul. 17, 2008

(65) Prior Publication Data
US 2010/0041723 A1    Feb. 18, 2010

(30) Foreign Application Priority Data

Jan. 8, 2007  (KR) ......................... 10-2007-0001935
Jan. 8, 2008  (KR) ......................... 10-2008-0001984

(51) Int. Cl.
*A61K 31/426* (2006.01)
(52) U.S. Cl. .................................................... 514/365
(58) Field of Classification Search .................. None
See application file for complete search history.

(56) References Cited

U.S. PATENT DOCUMENTS

| | | | |
|---|---|---|---|
| 6,710,063 B1 | 3/2004 | Chao et al. | |
| 7,105,551 B2 | 9/2006 | Cadilla et al. | |
| 7,153,878 B2 | 12/2006 | Conner et al. | |

FOREIGN PATENT DOCUMENTS

| | | | |
|---|---|---|---|
| WO | 01/00603 A1 | 1/2001 | |
| WO | 02/062774 A1 | 8/2002 | |
| WO | 03/072100 A1 | 9/2003 | |
| WO | 03/106442 A1 | 12/2003 | |
| WO | WO 2006091047 A1 * | 8/2006 | |

OTHER PUBLICATIONS

Issemann et al., "Activation of a Member of the Steroid Hormone Receptor Superfamily by Peroxisome Proliferators", Nature, Oct. 18, 1990, vol. 347, pp. 645-650.
Bennett et al., "Protein-Tyrosine-Phosphatase SHPTP2 Couples Platelet-Derived Growth Factor Receptor β to Ras", Proc. Natl. Acad. Sci. USA, Jul. 1994, vol. 91, pp. 7335-7339.
Palmer et al., "Peroxisome Proliferator Activated Receptor-α Expression in Human Liver", Mol. Pharmacol., 1998, vol. 53, pp. 14-22.
Lambe et al., "Species Differences in Sequence and Activity of the Peroxisome Proliferator Response Element (PPRE) Within the Acyl CoA Oxidase Gene Promoter", Toxicol. Lett., 1999, vol. 110, pp. 119-127.
Motojima et al., "Expression of Putative Fatty Acid Transporter Genes are Regulated by Peroxisome Proliferator-Activated Receptor α and γ Activators in a Tissue- and Inducer-Specific Manner", J. Biol. Chem., Jul. 3, 1998, vol. 273, No. 27, pp. 16710-16714.
Dreyer et al., "Positive Regulation of the Peroxisomal β-Oxidation Pathway by Fatty Acids Through Activation of Peroxisome Proliferator-Activated Receptors (PPAR)", Biol. Cell., 1993, vol. 77, pp. 67-76.
Peters et al., "Alterations in Lipoprotein Metabolism in Peroxisome Proliferator-Activated Receptor α-Deficient Mice", J. Biol. Chem., Oct. 24, 1997, vol. 272, No. 43, pp. 27307-27312.
Barak et al., "PPARγ is Required for Placental, Cardiac, and Adipose Tissue Development", Mol. Cell., Oct. 1999, vol. 4, pp. 585-595.
Lim et al., "Cyclo-Oxygenase-2-Derived Prostacyclin Mediates Embryo Implantation in the Mouse via PPARδ", Genes & Dev., 1999, vol. 13, pp. 1561-1574.
Kremarik-Bouillaud et al., "Regional Distribution of PPARβ in the Cerebellum of the Rat", J. Chem. Neuroanatomy, 2000, vol. 19, pp. 225-232.
Tan et al., "Critical Roles of PPARβ/δ in Keratinocyte Response to Inflammation", Genes & Dev., 2001, vol. 15, pp. 3263-3277.
Henson, "Suppression of Macrophage Inflammatory Responses by PPARs", Proc. Natl. Acad. Sci. USA, May 27, 2003, vol. 100, No. 11, pp. 6295-6296.
Barak et al., "Effects of Peroxisome Proliferator-Activated Receptor δ on Placentation, Adiposity, and Colorectal Cancer", Proc. Natl. Acad. Sci. USA, Jan. 8, 2002, vol. 99, No. 1, pp. 303-308.
Peters et al., "Growth, Adipose, Brain, and Skin Alterations Resulting from Targeted Disruption of the Mouse Peroxisome Proliferator-Activated Receptor β(δ)", Mol. & Cell. Biol , Jul. 2000, vol. 20, No. 14, pp. 5119-5128.
Clapham et al., "Mice Overexpressing Human Uncoupling Protein-3 in Skeletal Muscle are Hyperphagic and Lean", Nature, 2000, vol. 406, pp. 415-418.
Wang et al., "Peroxisome-Proliferator-Activated Receptor δ Activates Fat Metabolism to Prevent Obesity", Cell , Apr. 18, 2003, vol. 113, pp. 159-170.
Oliver et al., "A Selective Peroxisome Proliferator-Activated Receptor δ Agonist Promotes Reverse Cholesterol Transport," Proc. Natl. Acad. Sci. USA, Apr. 24, 2001, vol. 98, No. 9, pp. 5306-5311.
Lee et al., "Transcriptional Repression of Atherogenic Inflammation: Modulation by PPARδ", Science, Oct. 17, 2003, vol. 302, pp. 453-457.

(Continued)

*Primary Examiner* — Kamal Saeed
*Assistant Examiner* — Nyeemah A Grazier
(74) *Attorney, Agent, or Firm* — The Webb Law Firm

(57) ABSTRACT

The present invention relates to a thiazole compound as a peroxisome proliferator activated receptor δ (PPARδ) activator or pharmaceutically acceptable salts thereof, and a pharmaceutical composition, a functional cosmetic composition, a health food, health beverages, a food additive and animal feeds containing the same.

1 Claim, No Drawings

OTHER PUBLICATIONS

Wang et al., "Regulation of Muscle Fiber Type and Running Endurance by PPARδ", PLoS Biology, Oct. 2004, vol. 2, issue 10:e294, pp. 1532-1539.

Liu et al., "Memory Loss in Old Rats is Associated with Brain Mitochondrial Decay and RNA/DNA Oxidation: Partial Reversal by Feeding Acetyl-L-Carnitine and/or R-α-Lipoic Acid", Proc. Natl. Acad. Sci. USA, Feb. 19, 2002, vol. 99, No. 4, pp. 2356-2361.

Johnson et al., "Structural Requirements and Cell-Type Specificity for Ligand Activation of Peroxisome Proliferator-Activated Receptors", J. Steroid Biochem. Mol. Biol., 1997, vol. 63, No. 1-3, pp. 1-8.

Brooks et al., "Modulators of Leukotriene Biosynthesis and Receptor Activation", J.Med. Chem., Jul. 5, 1996, vol. 39, No. 14, pp. 2629-2654.

Brown et al., "Identification of Peroxisome Proliferator-Activated Receptor Ligands from a Biased Chemical Library", Chem. Biol., 1997, vol. 4, No. 12, pp. 909-918.

Tanaka et al., "Activation of Peroxisome Proliferator-Activated Receptor δ Induces Fatty Acid β-Oxidation in Skeletal Muscle and Attenuates Metabolic Syndrome", Proc. Natl. Acad. Sci. USA, Dec. 23, 2003, vol. 100, No. 26, pp. 15924-15929.

Lee et al., "PAARδ Regulates Glucose Metabolism and Insulin Sensitivity", Proc. Natl. Acad. Sci. USA, Feb. 28, 2006, vol. 103, No. 9, pp. 3444-3449.

Kubota et al., "PPARγ Mediates High-Fat Diet-Induced Adipocyte Hypertrophy and Insulin Resistance", Mol. Cell, Oct. 1999, vol. 4, pp. 597-609.

Rosen et al., "PPARγ is Required for the Differentiation of Adipose Tissue in Vivo and in Vitro", Mol. Cell, Oct. 1999, vol. 4, pp. 611-617.

Lambert et al., "The ORD1 Gene Encodes a Transcription Factor Involved in Oxygen Regulation and is Identical to IXR1, a Gene That Confers Cisplatin Sensitivity to *Saccharomyces cerevisiae*", Proc. Natl. Acad. Sci. USA, Jul. 1994, vol. 91, pp. 7345-7349.

Gottschalk et al., "Identification of Immunosuppressant-Induced Apoptosis in a Murine B-Cell Line and its Prevention by Bcl-x but not Bcl-2", Proc. Natl. Acad. Sci. USA, Jul. 1994, vol. 91, pp. 7350-7354.

Kliewer et al., "Differential Expression and Activation of a Family of Murine Peroxisome Proliferator-Activated Receptors", Proc. Natl. Acad. Sci. USA, Jul. 1994, vol. 91, pp. 7355-7359.

Yong-Xu Wang et al., "Regulation of Muscle Fiber Type and Running Endurance by PPARδ", PLoS Biology, vol. 2, Issue 10, pp. 1532-1539.

Jiankang Liu, et al., "Memory Loss in Old Rats is Associated with Brain Mitochondrial Decay and RNA/DNA Oxidation: Partial Reversal by Feeding Acetyl-L-Carnitine and/or R-α-lipoic Acid", PNAS, vol. 99, Issue 4, pp. 2356-2361.

Office Action dated Aug. 15, 2011 for corresponding Chinese Application No. 200880001841 and English language translation thereof.

\* cited by examiner

THIAZOLE COMPOUND (AS PPARδ) LIGAND AND PHARMACEUTICAL, COSMETIC AND HEALTH FOOD COMPRISED THEREOF

TECHNICAL FIELD

The present invention relates to the thiazole compound represented by formula 1 as a PPARδ (Peroxisome Proliferator Activated Receptor δ) ligand which can be used for the treatment of obesity, hyperlipidemia, arteriosclerosis, diabetes, dementia, Alzheimer's and Parkinson's disease, and used for strengthening muscles or improving memory and a pharmaceutical composition, a cosmetic composition, a health food, health beverages, a food additive and animal feeds containing the same.

[Formula 1]

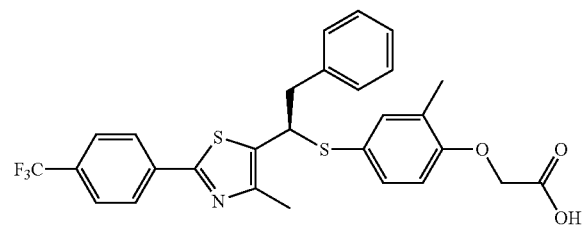

BACKGROUND ART

Among nuclear receptors, PPAR (Peroxisome Proliferator Activated Receptor) is known to have three subtypes, which are PPARα, PPARγ and PPARδ (*Nature,* 1990, 347, p 645-650, *Proc. Natl. Acad. Sci. USA* 1994, 91, p 7335-7359). PPARα, PPARγ and PPARδ have tissue-specific functions in vivo and different regions for expression. PPARα is mainly expressed in the heart, kidney, skeletal muscle and large intestines in humans (*Mol. Pharmacol.* 1998, 53, p 14-22, *Toxicol. Lett.* 1999, 110, p 119-127, *J. Biol. Chem.* 1998, 273, p 16710-16714), and is involved in β-oxidation of peroxisome and mitochondria (*Biol. Cell.* 1993, 77, p 67-76, *J. Biol. Chem.* 1997, 272, p 27307-27312). PPARγ is expressed in the skeletal muscle at a low level, but mainly expressed in the adipose tissue to induce the adipocyte differentiation and to store energy as a form of fat, and is involved in homeostatic regulation of insulin and glucose (*Moll. Cell.* 1999, 4, p 585-594, p 597-609, p 611-617). PPARδ is preserved evolutionarily in mammals including humans and vertebrates including rodents and sea squirts. The previous studies confirmed that PPARδ plays an important role in the reproductive cell expression (*Genes Dev.* 1999, 13, p 1561-1574) and has physiological functions of differentiating neuronal cells (*J. Chem. Neuroanat* 2000, 19, p 225-232) in central nervous system (CNS) and wound healing with anti-inflammatory effect (*Genes Dev.* 2001, 15, p 3263-3277, *Proc. Natl. Acad. Sci. USA* 2003, 100, p 6295-6296). Recent studies also confirmed that PPARδ is involved in the adipocyte differentiation and lipid metabolism (*Proc. Natl. Acad. Sci. USA* 2002, 99, p 303-308, *Mol. Cell. Biol.* 2000, 20, p 5119-5128). For example, PPARδ activates the expression of key gene involved in β-oxidation in fatty acid catabolism and uncoupling proteins (UCPs), the gene involved in energy metabolism, which brings the effect of improving obesity (*Nature* 2000, 406, p 415-418, *Cell* 2003, 113, p 159-170). The activation of PPARδ increases the HDL (High Density Lipoprotein) level, improves type 2 diabetes without weight changes (*Proc. Natl. Acad. Sci. USA* 2001, 98, p 5306-5311, 2003, 100, p 15924-15929, 2006, 103, p 3444-3449), and favors the treatment of arteriosclerosis by inhibiting the gene associated with arteriosclerosis (*Science,* 2003, 302, p 453-457). Therefore, PPARδ ligand can be developed as a drug for the treatment of metabolic diseases such as obesity, diabetes, hyperlipidemia and arteriosclerosis.

PPARδ regulates mitochondria biosynthesis. When PPARδ was artificially over-expressed in the mouse muscles, mitochondria biosynthesis was increased and Type I muscle fiber was increased significantly, in addition to the increase of fatty acid β oxidase. Therefore, constant running time and distance were respectively 67% and 92% increased, compared with wild type mouse (*PLoS Biology,* 2004, 2:e294). The increase of mitochondria biosynthesis has a positive effect on the enhancement of brain functions. If mitochondria in brain cell is destroyed by oxidative stress, memory decreases significantly (*Proc. Natl. Acad. Sci. USA* 2002, 99, p 2356-2361). Dementia, Alzheimer's and Parkinson's disease are the representative degenerative diseases, which demonstrate significant decrease of learning and memory. Therefore, the mitochondria proliferating agent developed in the present invention not only contributes to the improvement of memory, but also can be developed as a therapeutic agent for Alzheimer's and and Parkinson's disease.

Synthetic PPARδ ligands developed, so far, have less selectivity, compared with other PPARα and PPARγ ligands. The early selective ligand was L-631033, developed by Merk (*J. Steroid Biochem. Mol. Biol.* 1997, 63, p 1-8), which was produced by introducing a functional group being able to fix side chain based on its natural fatty acid morphology. The same research team reported later more effective ligand L-165041 (*J. Med. Chem.* 1996, 39, p 2629-2654), in which the compound known as a leukotriene agonist is functioning to activate human PPARδ. This compound exhibited great selectivity to hPPARδ, which is 10 times the selectivity to PPARα or PPARγ. And $EC_{50}$ of the compound was 530 nM. Other ligands L-796449 and L-783483 have improved affinity ($EC_{50}$=7.9 nM), but barely have selectivity to other hPPAR subtypes.

Glaxo-Smith-Kline reported GW2433 (*Chem. Biol.* 1997, 4, p 909-918), the PPARα activator, which is Y-type ligand having a similar structure to the crystal structure of the PPARδ ligand pocket. Unlike the conventional ligands known so far, this ligand has Y-type structure containing benzene ring, which favors spatial binding to the PPARδ ligand pocket. However, this ligand is a double-active ligand having activity to hPPARα as well, suggesting that selectivity to PPARδ is reduced. The PPARδ selective ligand GW501516 ([2-methyl-4-[[[4-methyl-2-[4-(trifluoromethyl)phenyl]-1, 3-thiazol-5-yl]methyl]sulfanyl]phenoxy]acetic acid), recently developed by GlaxoSmithKline, exhibits much better physiological effect than any other ligands previously developed (*Proc. Natl. Acad. Sci. USA* 2001, 98, p 5306-5311).

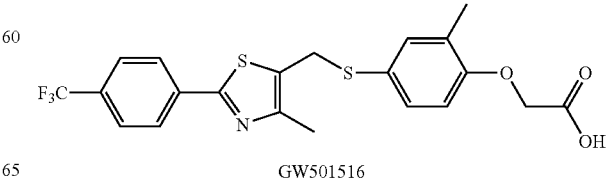

GW501516

The GW501516 has excellent affinity (1-10 nM) to PPARδ, and excellent selectivity to PPARα or PPARγ as well, which is at least 1000 times the selectivity of earlier ligands.

However, the PPARδ activity induced by all the ligands developed so far is only resulted from 30-40% of total ligand-binding pockets.

WO 2001-00603 applied by Glaxo group describes the compound represented by the following formula A containing the GW501516 as a selective activator of PPARδ. However, this description includes only a part of the test results of GW501516 using Rhesus model.

formula A

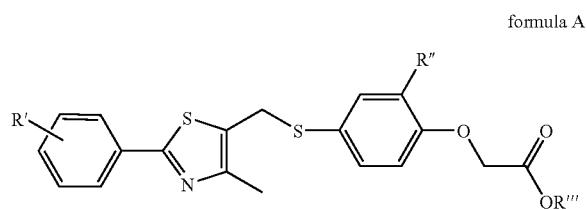

[Wherein, R' is $CF_3$ or F, R" is H, $CH_3$ or Cl, and R'" is H, $CH_3$ or $CH_2CH_3$.]

The thiazole compound represented by formula B as a PPARδ selective activator has been described in WO 2002-62774 applied by Glaxo group.

formula B

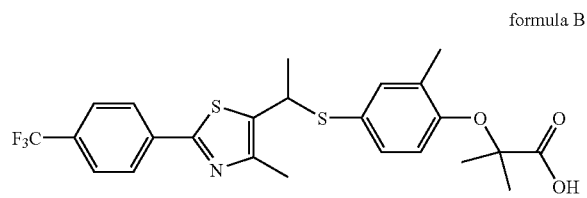

WO 2003-072100 applied by Eli Lilly describes a pharmaceutical composition for selective regulation of PPARδ containing the compound represented by the following formula C.

formula C

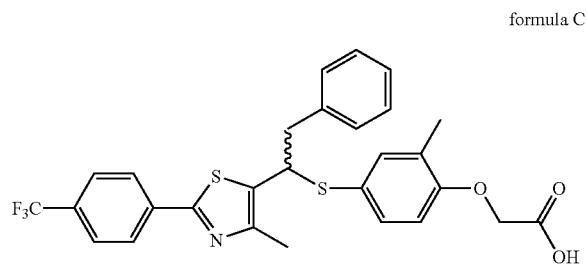

However, the description only declares that the composition has been prepared, which is produced as a racemate not as an optical isomer comprising two types. And the document only describes $M^++1$ value of mass spectrometry of the produced racemate, which is confirmed by $^1$H-NMR and acts as a selective activator of PPARδ, but does not mention about the pharmacological effect as a selective activator of PPARδ.

DISCLOSURE

Technical Problem

The present inventors prepared an optical-active compound having high PPARδ selectivity among racemic compounds of the thiazole derivative described in WO 2003-072100. Therefore, the object of the present invention is to provide the optical-active compound having high PPARδ selectivity and a pharmaceutical composition, a functional cosmetic composition, and a composition for health food and animal feeds containing the optical-active compound of the thiazole derivative.

Technical Solution

The present invention relates to the thiazole compound represented by formula 1 as a PPARδ (Peroxisome Proliferator Activated Receptor δ) ligand which can be used for the treatment of obesity, hyperlipidemia, arteriosclerosis, diabetes, dementia, Alzheimer's and Parkinson's disease and for strengthening muscles or improving memory, and a pharmaceutical composition, a cosmetic composition, and a composition for health food and animal feeds containing the same.

[Formula 1]

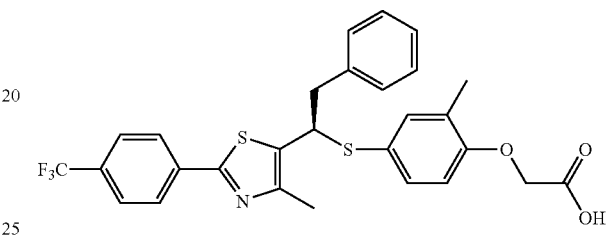

WO 2003-072100 describes the thiazole compound represented by formula C. But, it only describes $M^++1$ value of mass spectrometry of the produced racemate, which is confirmed by $^1$H-NMR and acts as a selective activator of PPARδ; it does not describe the pharmacological effect as a selective activator of PPARδ.

formula C

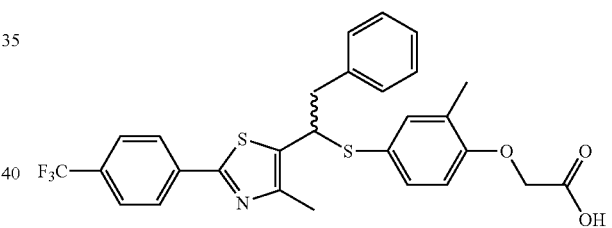

The above compound of formula C contains a chiral carbon and thus there are stereoisomers thereof.

The present inventors confirmed that the R-form isomer represented by formula 1, the optical active isomer of the racemic compound of the formula C, has high selective activity to PPARδ but the S-form isomer represented by formula 2 shows significantly reduced activity to PPARδ.

[Formula 2]

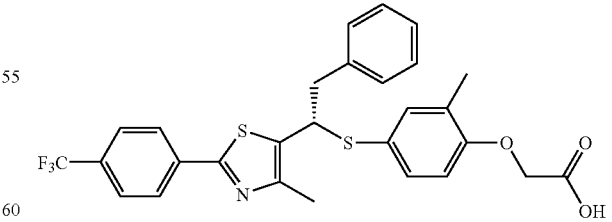

So, the compound of formula 1 of the present invention is regarded as a selective invention of WO 2003-072100.

The compound represented by formula 1 of the present invention can be prepared by the following reaction formula 1.

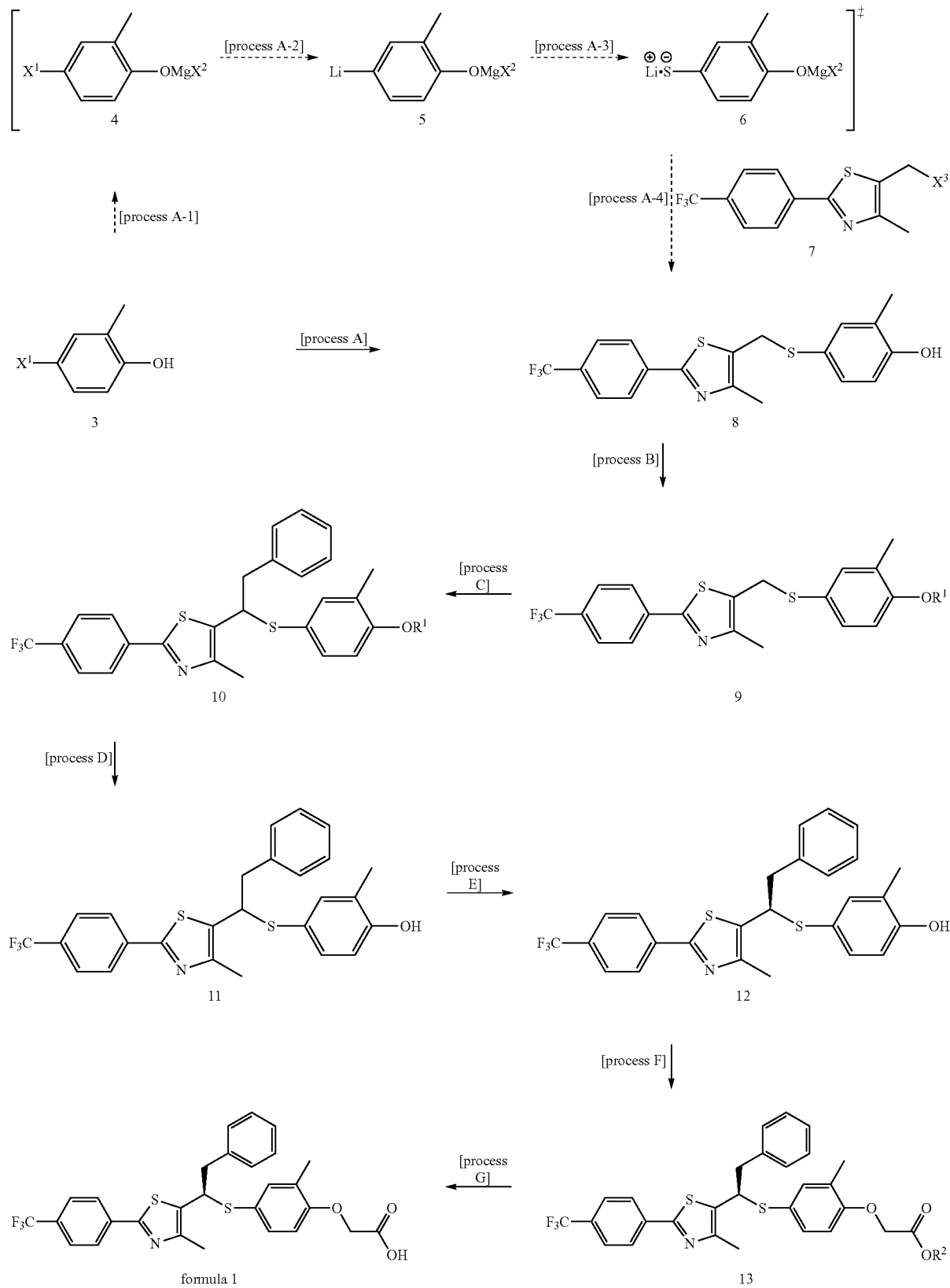

[Wherein, $R^1$ is phenol protecting group, which can be C1-C4 lower alkyl, allyl, alkylsilyl, alkylarylsilyl or tetrahydropyranyl; $R^2$ is carboxylic acid protecting group containing C1-C4 alkyl or allyl; $X^1$ is bromine atom or iodine atom; $X^2$ and $X^3$ are independently chlorine atom, bromine atom, iodine atom or leaving group having reactivity with nucleophilic substitution.]

Hereinafter, the preparation method of the invention is described in detail. However, the following descriptions cannot limit the scope nor the spirit of the invention.

[Process A] Preparation of the Compound Represented by Formula 8

To prepare the compound represented by formula 8, 4-halo-2-methylphenol, the compound represented by formula 3 was treated with Grignard reagent to protect phenol group without an independent separation process, and reacted with an organic metal reagent and S stepwise, and finally reacted with the compound represented by formula 7. This process has 4 sub-reaction stages performed in a row.

The sub-reaction stages are described in detail hereinafter.

(Process A-1): The anhydride solvent used in this process is selected from the group consisting of such single solvents as diethylether, tetrahydrofuran, hexane and heptane and mixed solvents comprising at least two of these solvents. It is more preferred to select diethylether, tetrahydrofuran or the mixed solvent comprising diethylether and tetrahydrofuran as the anhydride solvent.

Grignard reagent used herein can be selected from the group consisting of methyl, ethyl, n-propyl, iso-propyl, n-butyl, sec-butylmagnesiumchloride ($R_2MgCl$) and alkylmagnesiumbromide ($R_2MgBr$). Among these, iso-propylmagnesiumchloride [$(CH_3)_2CHMgCl$] is most preferred.

The reaction temperature depends on a solvent, but it is generally set at –20~40° C. and preferably at 0° C.~room temperature (25° C.). The reaction time depends on the reaction temperature and a solvent, but it is generally 10-60 minutes and preferably 10-30 minutes.

(Process A-2 and Process A-3): The organic metal reagent used for halogen-lithium substitution can be selected from the group consisting of n-butyl lithium, sec-butyl lithium and tert-butyl lithium. Among these compounds, tert-butyl lithium is most preferred.

S with fine particles is preferred, which is added in a solvent directly.

The reaction temperature depends on a solvent, but is generally set at –78~25° C. The reaction temperature for halogen-metal substitution is preferably –75° C. and the temperature for S introduction is –75~room temperature (25° C.) The halogen-metal substitution reaction takes 10-30 minutes and the S introduction reaction takes 30-90 minutes.

(Process A-4): 5-halogenmethyl-4-methyl-2[4-(trifluoromethyl)phenyl]thiazole, the compound represented by formula 7 used in this process was prepared by the known method (WO 03/106442). Halogen of the compound represented by formula 7 is selected from the group consisting of chlorine, bromine and iodine. And among these, chlorine is most preferred.

The reaction temperature depends on a solvent, but it is generally set at –78~25° C., more preferably at 0~10° C. The reaction time is generally 10-120 minutes and preferably 10-60 minutes.

[Process B] Preparation of the Compound Represented by Formula 9

To prepare the compound represented by formula 9, the compound represented by formula 8 is preferably reacted with the compound generally used as phenol protecting group in the presence of base.

The aprotic polar solvent used in this process is selected from the group consisting of N,N-dimethylformamide, N,N-dimethylacetamide, dimethylsilfoxide, acetonitrile, acetone, ethylacetate, carbon tetrachloride, chloroform and dichloromethane. The ether herein can be selected from the group consisting of tetrahydrofuran, dioxane, dimethoxyethane, diethyleneglycoldimethylether and triethyleneglycoldimethylether. The aromatic hydrocarbon is exemplified by benzene, toluene and xylene. As a solvent herein, the aprotic polar solvent is preferred and particularly N,N-dimethylformamide, chloroform or dichloromethane is more preferred.

The base herein is amine including pyridine, triethylamine, imidazole and N,N-dimethylaminopyridine. For the reaction of alkyl or allyl etherified protecting group, such bases as sodium hydroxide, potassium hydroxide, sodium carbonate and potassium carbonate are used. In particular, imidazole and potassium carbonate are more preferred.

Alkylsilylhalide or alkylarylsilylhalide is used as the silyl protecting group and 3,4-dihydro-2H-pyrane is used as the tetrahydropyranyl protecting group.

The reaction temperature depends on a solvent, but it is generally set at 10~80° C., more preferably at 0~room temperature (25° C.). The reaction time depends on the reaction temperature and a solvent, but generally, it takes from one hour to one day. It is more preferred to finish the reaction within 4 hours.

[Process C] Preparation of the Compound Represented by Formula 10

To prepare the compound represented by formula 10, α-proton of thioether of the compound represented by formula 9 is treated with a strong alkali to give a nucleophile, which is reacted with various electrophiles.

The anhydride solvent used in this process is selected from the group consisting of such single solvents as diethylether, tetrahydrofuran, hexane and heptane and mixed solvents comprising at least two of these solvents. It is more preferred to select diethylether, tetrahydrofuran or the mixed solvent comprising diethylether and tetrahydrofuran as the anhydride solvent.

The strong alkali used for the a-proton extraction is selected from the group consisting of potassium tert-butoxide (t-BuOK), lithium diisopropyl amide (LDA), n-butyl lithium, sec-butyl lithium and tert-butyl lithium, and among these compounds, lithium diisopropyl amide (LDA) is most preferred.

The electrophile reacted with the nucleophile of thioether is benzylhalide.

The reaction temperature depends on a solvent, but is generally –78~25° C. It is more preferred to perform the α-proton extraction reaction in the presence of a strong alkali at –75° C. at which electrophile is added. Then, the temperature is raised slowly to room temperature (25° C.). The reaction time differs from each reaction stage. For example, the α-proton extraction by a strong alkali takes 10-30 minutes and the reaction with electrophile takes 30-90 minutes.

[Process D] Preparation of the Compound Represented by Formula 11

The compound represented by formula 11 is obtained by eliminating the phenol protecting group from the compound represented by formula 10.

The polar solvent used in this process is selected from the group consisting of N,N-dimethylformamide, N,N-dimethylacetamide, dimethylsilfoxide, acetonitrile, acetone, ethylacetate, carbon tetrachloride, chloroform and dichloromethane. The ether herein can be selected from the group consisting of tetrahydrofuran, dioxane, dimethoxyethane and diethyleneglycoldimethylether. The alcohol can be methanol or ethanol.

The aromatic hydrocarbon is exemplified by benzene, toluene and xylene. As a solvent herein, the polar solvent is preferred and particularly tetrahydrofuran is more preferred.

To eliminate the phenol protecting group, particularly to eliminate methyl, ethyl, tert-butyl, benzyl or allylether protecting group, trimethylsilyliodide, ethanethioalcoholsodium salt, lithiumiodide, aluminum halide, boron halide or Lewis acid such as trifluoroacetic acid is used, and to eliminate the silyl protecting group such as trimethylsilyl, tert-butyldiphenylsilyl, triisopropylsilyl and tert-butyldimethylsilyl, fluoride such as tetrabutylammoniumfluorine ($Bu_4N^+F^-$), halogen acid (hydrofluoric acid, hydrochloric acid, hydrobromic acid or hydroiodic acid) or potassium fluoride is used. It is preferred to use fluoride to eliminate the silyl protecting group and is more preferred to use tetrabutylammoniumfluorine.

The reaction temperature depends on a method and a solvent but is generally 0~120° C. and preferably 10~25° C. The reaction time depends on the reaction temperature, but generally it takes from 30 minutes to one day. It is more preferred to finish the reaction within 2 hours.

[Process E] Preparation of the Compound Represented by Formula 12

The compound is prepared by separating the R-isomer represented by formula 12 and another isomer S-isomer from the racemic compound of formula 11. This separation is performed by HPLC using a chiral normal phase column. At this time, the solvent is the mixed solvent comprising non-polar solvents such as hexane, heptane and pentane and polar solvents such as ethanol and isopropyl alcohol.

[Process F] Preparation of the Compound Represented by Formula 13

To prepare the compound represented by formula 13, the compound represented by formula 12 is preferably reacted with halogenacetate alkylester or halogenacetate allylester in the presence of base.

The halogenacetate alkylester or halogenacetate allylester is the general compound that can be easily obtained. The halogen herein is exemplified by chlorine atom, bromine atom and iodine atom. Preferably, bromoacetate methylester, bromoacetate allylester or bromoacetate ethylester is used as the halogenacetate alkylester or halogenacetate allylester.

The solvent used in this process can be a soluble single solvent selected from the group consisting of N,N-dimethylformamide, N,N-dimethylacetamide, dimethylsulfoxide, acetonitrile, acetone, ethanol and methanol or a mixed solvent prepared by mixing these solvents with 1-10% water. The most preferred solvent is the mixed solvent prepared by mixing acetone or dimethylsulfoxide with 1-5% water.

The base used in this process is not limited as long as it does not have a bad influence on the reaction, regardless of strong or weak, which is exemplified by alkali metal hydride such as sodium hydride and lithium hydride, alkali earth metal hydride such as potassium hydride, alkali metal hydroxide such as sodium hydroxide and potassium hydroxide, and alkali metal carbonate such as lithium carbonate, potassium carbonate, potassium bicarbonate and cesium carbonate. Among these compounds, alkali metal carbonate is preferred, and potassium carbonate is more preferred.

The reaction temperature is not limited, but only up to the boiling point of a solvent. However, high temperature is not preferred to inhibit side reactions. The preferable reaction temperature is 0~60° C. The reaction time differs from the reaction temperature, but is generally 30 minutes-1 day and preferably 30-90 minutes.

[Process G] Preparation of the Compound Represented by Formula 1

The compound represented by formula 1 is prepared from the compound represented by formula 13 by hydrolyzing carboxylic acid ester of the compound in the mixed solution of soluble inorganic salt and alcohol or salts are prepared from allyl ester in the presence of a palladium catalyst.

The solvent used in this process is a soluble solvent that can be mixed with water, for example alcohol such as methanol and ethanol. The inorganic salt used in this process is an aqueous solution prepared by mixing alkali metal hydroxide such as lithium hydroxide, sodium hydroxide and potassium hydroxide with water at the concentration of 0.1-3 N, considering the type of carboxylic acid alkali salt. The acid used to obtain the compound represented by formula 13 as a carboxylic acid form is preferably acetic acid aqueous solution or 0.1-3 N hydrochloric acid aqueous solution.

The reaction is preferably performed at a low temperature in order to inhibit side reactions, which is generally 0° C.-room temperature. The reaction time depends on the reaction temperature, but is generally 10 minutes-3 hours and more preferably 30 minutes-1 hour.

The pharmaceutically acceptable salt of the compound represented by formula 1 is prepared by allyl ester salt substitution from the compound represented by formula 13 using palladiumtetrakistriphenylphosphine catalyst and metal salt according to the reaction formula 2. The solvent used in this process is selected from the group consisting of chloroform, carbon tetrachloride, dichloromethane, tetrahydrofuran and ethylacetate. The catalyst used in this process is paladiumtetrakistriphenylphosphine. The salt for the salt substitution is potassium 2-ethylhexanoate or sodium 2-ethylhexanoate.

[Reaction Formula 2]

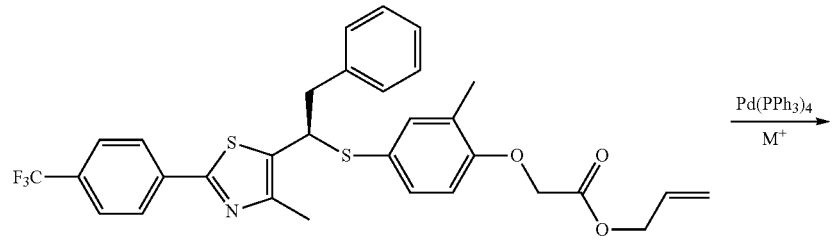

-continued

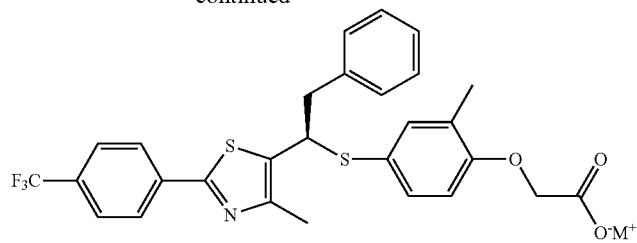

The resultant compound containing S represented by formula 1 is a very important material as a PPARδ protein ligand.

The present invention includes the compound represented by formula 1, solvates and salts thereof, which can be effectively used as a Peroxisome Proliferator Activated Receptor δ (PPARδ) activator composition. Precisely, the compound represented by formula 1 of the present invention and pharmaceutically acceptable salts thereof can be very effective as a pharmaceutical composition for the treatment and prevention of arteriosclerosis or hyperlipidemia; for increasing high density lipoprotein (HDL); for the treatment and prevention of diabetes; for the treatment and prevention of obesity; for strengthening muscle or enhancing endurance; for improving memory; for the treatment and prevention of dementia or Parkinson's disease; and a composition for health food supplements, health beverages, food additives and animal feeds. The compound represented by formula 1 or pharmaceutically acceptable salts thereof of the present invention can be used for the functional cosmetic composition for prevention and improvement of obesity and for the functional cosmetic composition for strengthening muscle and enhancing endurance. The functional cosmetic composition for strengthening muscle and enhancing endurance can be formulated as ointment, lotion, cream or gel to be applied on the body part before/after exercise and can be used for a long term to bring the wanted effect. The compound represented by formula 1 or pharmaceutically acceptable salts thereof of the present invention can be formulated as ointment and be applied on the body part to prevent or treat diabetes or diabetic foot ulcer, so-called diabetic ulcer.

The present invention also provides a peroxisome proliferator activated receptor δ (PPARδ) activator composition containing the thiazole compound represented by formula 1 or pharmaceutically acceptable salts thereof as an active ingredient.

The pharmaceutically acceptable salt herein includes all the salts that are able to form salt with carboxylic acid of the compound of formula 1 and alkali metal ions or alkali earth metal ions, which are exemplified by $Li^+$, $Na^+$, $K^+$, $Ca^{2+}$, etc.

The effective dose of the compound represented by formula 1 or pharmaceutically acceptable salts thereof of the present invention can be determined according to the type of compound, administration method, target subject and target disease, but is determined based on the conventional medicinal standard. The preferable dose of the compound represented by formula 1 is 1-100 mg/kg (body weight)/day. The administration frequency can be once or several times a day within the allowed one day dosage. The composition of the present invention can be administered orally or parenterally and be used in general forms of pharmaceutical formulation. For example, the composition of the present invention can be formulated as tablets, powders, dried syrups, chewable tablets, granules, capsules, soft capsules, pills, drinks, sublinguals, etc. The tablets of the present invention can be administered to a subject by a method or pathway that delivers the effective dose of the tablet with bioavailability, which is the oral. pathway. And the administration method or the pathway can be determined according to the characteristics, stages of the target disease and other conditions. When the composition of the present invention is formed as tablets, it can additionally include one or more pharmaceutically acceptable excipients. The content and characteristics of the excipient can be determined by the solubility and chemical properties of the selected tablet, administration pathway and standard pharmaceutical practice.

The compound of formula 1 of the present invention can be added to health food supplements or health beverages for the prevention and improvement of hyperlipidemia; for increasing high density lipoprotein (HDL); for the prevention and improvement of diabetes; for the prevention and improvement of obesity; for strengthening muscle or for enhancing endurance; for improving memory; for the prevention and improvement of dementia or Parkinson's disease. At this time, the content of the compound in those health food and beverages can be adjusted according to the purpose and application. In addition to the ingredients mentioned above, the compound represented by formula 1 of the present invention can include in variety of nutrients, vitamins, minerals (electrolytes), flavors including natural flavors and synthetic flavors, coloring agents and extenders (cheese, chocolate, etc.), pectic acid and its salts, alginic acid and its salts, organic acid, protective colloidal viscosifiers, pH regulators, stabilizers, antiseptics, glycerin, alcohols, carbonators which are used to be added to soda, etc.

Best Mode

Practical and presently preferred embodiments of the present invention are illustrated as shown in the following Examples.

However, it will be appreciated that those skilled in the art, on consideration of this disclosure, may make modifications and improvements within the spirit and scope of the present invention.

EXAMPLE 1

Preparation of the Compound of Formula 8 (Process A)

500 mg (2.14 mmol) of 4-iodo-2-methylphenol was dissolved in 20 ml of anhydride tetrahydrofuran in the presence of nitrogen and, at that time, temperature was maintained at 0° C. 1.1 ml of isopropylmagnesiumchloride (2 M-ether solution, 2.16 mmol) was slowly added thereto, followed by reaction for 10 minutes. The reaction solution was cooled down to −78° C., to which 2.77 ml of tert-butyl lithium (1.7 M-heptane solution, 4.70 mmol) was slowly added. After reacting for 20 minutes, 69 mg of S (2.14 mmol) was slowly added thereto, followed by further reaction until the temperature of the reactant reached 15° C. 40 minutes later, 624 mg (2.14 mmol) of 5-chloromethyl-4-methyl-2-[(4-trifluoromethyl)phenyl]-thiazole represented by formula 7 was dissolved in 2 ml of anhydride THF, which was slowly added thereto at the same temperature. After one more hour of reaction, the reaction was terminated by adding 20 ml of ammonium chloride solution. The organic layer was separated and dried over magnesium sulfate. After filtering, the solvent was distillated under reduced pressure, and the residue was purified by silica gel column chromatography (hexane/ethyl acetate=3/1, v/v) to give 728 mg (yield: 86%) of the target compound.

$^1$H NMR(300 MHz, CDCl$_3$) δ 7.96 (d, 2H, J=8.1 Hz), 7.65(d, 2H, J=8.3 Hz), 7.19 (d, 1H, J=1.5 Hz), 7.01 (dd, 1H, J=8.2, 2.0 Hz), 6.62 (d, 1H, J=8.2 Hz), 5.86 (brs, 1H), 4.07 (s, 2H), 2.19 (s, 3H), 2.12(s, 3H)

$^{13}$C NMR(75.5 MHz, CDCl$_3$) δ 163.9, 155.5, 151.7, 137.4, 136.9, 133.5. 131.9 (q, J=32.6 Hz), 131.7, 126.8, 126.3, (q, J=3.9 Hz), 125.8, 123.8, 115.7, 33.2, 16.2, 14.8

EXAMPLE 2

Preparation of the Compound of Formula 9 (R$^1$=t-Bu(CH$_3$)$_2$Si—, Process B)

500 mg (1.26 mmol) of the compound of formula 8 and 171 mg (2.52 mmol) of imidazole were completely dissolved in 5 ml of dimethylformamide. 209 mg (1.38 mmol) of tert-butyldimethylsilylchloride was slowly added thereto, followed by stirring at room temperature for 4 hours. Upon completion of the reaction, the organic solvent was extracted by using ammonium chloride solution and ethyl acetate. Moisture of the organic layer was dried over magnesium sulfate. After filtering, the solvent was distillated under reduced pressure, and the residue was purified by silica gel column chromatography (hexane/ethyl acetate=10/1, v/v) to give 610 mg (yield: 95%) of the target compound.

$^1$H NMR (300 MHz, CDCl$_3$): 7.97 (d, 2H, J=8.1 Hz), 7.65 (d, 2H, J=8.2 Hz), 7.19 (d, 1H, J=1.9 Hz) 7.07 (m, 1H), 6.69 (d, 1H, J=8.3 Hz), 4.11 (s, 2H), 2.21 (s, 3H), 2.11 (S, 3H), 1.01 (S, 9H), 0.21 (s, 6H) $^{13}$C NMR (75.5 MHz, CDCl$_3$): δ 163.2, 154.7, 151.5, 137.1, 136.6, 133.3, 132.4, 131.7, 131.2, 131.0, 130.2, 129.2, 126.6, 126.1, 126.06, 126.01, 125.9, 124.9, 119.4, 32.8, 25.9, 18.5, 16.9, 15.0, −4.0

EXAMPLE 3

Preparation of the Compound of Formula 10 (R$^1$=t-Bu(CH$_3$)$_2$Si—, Process C)

300 mg (0.59 mmol) of the compound (R$^1$=t-Bu(CH$_3$)$_2$—) of formula 9 prepared in Example 2 was dissolved in 5 ml of anhydride tetrahydrofuran in the presence of nitrogen and the temperature was lowered to −78° C. 619 µl (2.0 M ether solution, 1.24 mmol) of lithium diisopropyl amide solution was slowly added thereto, followed by reaction for 10 minutes. Then, 77 µl (0.65 mmol) of benzylbromide was added to the reaction solution, followed by stirring for 30 minutes at the same temperature (−78° C.). The reaction was terminated by adding 5 ml of ammonium chloride solution. Moisture of the organic layer was dried over magnesium sulfate. After filtering, the solvent was distillated under reduced pressure, and the residue was purified by silica gel column chromatography (hexane/ethyl acetate=10/1, v/v) to give 265 mg (yield: 75%) of the target compound.

$^1$H NMR (300 MHz, CDCl$_3$): δ 7.97 (d, 2H, J=8.1 Hz), 7.65 (d, 2H, J=8.2Hz), 7.03-7.26 (m, 7H) 6.63 (d, 1H, J=8.3 Hz), 4.51 (dd, 1H, J=9.8, 5.3 Hz), 3.37 (dd, 1H, J=9.8, 5.3 Hz), 3.05 (dd, 1H, J=13.6, 9.9 Hz), 2.10 (s, 3H), 1.83 (s, 3H), 0.98 (s, 9H) , 0.18 (s, 6H) 13C NMR (75 MHz, CDCl3): δ 163.5, 155.1, 151.8, 138.4, 137.7, 136.5, 133.5, 130.3, 129.3, 128.9, 127.2, 126.8, 126.7, 126.2, 126.1, 124.5, 119.4, 49.2, 44.4, 26.1, 18.7, 17.1, 15.1, −3.81, −3.84

EXAMPLE 4

Preparation of the Compound of Formula 11 (Process D)

200 mg (0.33 mmol) of the compound (R$^1$=t-Bu(CH$_3$)$_2$Si—) of formula 10 prepared in Example 3 was dissolved in 5 ml of anhydride tetrahydrofuran in the presence of nitrogen. 660 µl (0.66 mmol) of tetrabutylammoniumfluoride 1 M tetrahydrofuran solution was slowly added thereto at room temperature, followed by stirring for 1 hour. Upon completion of the reaction, the organic layer was separated by adding ethyl acetate and water. Moisture of the organic layer was dried over magnesium sulfate. After filtering, the solvent was distillated under reduced pressure, and the residue was purified by silica gel column chromatography (hexane/ethyl acetate=5/1, v/v) to give 146 mg (yield: 91%) of the target compound.

$^1$H NMR (500 MHz, CDCl$_3$): δ 7.92 (d, 2H, J=8.2 Hz), 7.50 (s, 1H), 7.59 (d, 2H, J=8.2Hz), 7.07-7.22 (m, 6H), 6.85 (m, 1H), 6.44 (d, 1H, J=8.2 Hz), 4.47 (dd, 1H, J=9.7, 5.4 Hz), 3.39 (dd, 1H, J=13.8, 5.4 Hz), 3.06 (dd, 1H, J=13.8, 9.8 Hz), 2.12 (s, 3H), 1.73 (s, 3H) $^{13}$C NMR (125 MHz, CDCl3): δ 164.1, 155.7, 151.2, 138.0, 137.9, 137.0, 136.4, 133.8, 131.8, 131.5, 129.0, 128.6, 127.2, 127.0, 126.6, 126.14, 126.11, 125.7, 125.0, 122.9, 122.7, 115.2, 60.8, 49.1, 43.7, 21.2, 15.9, 14.3, 14.2

EXAMPLE 5

Preparation of the Compound of Formula 12 (Process E)

90 mg of the compound of formula 11 prepared in Example 4 proceeded to semiprep chiral HPLC column (chiralpack AD-H) to give 45 mg of the target compound represented by formula 12 in R-form and 45 mg of its corresponding isomer in S-form.

Moving phase: hexane/isopropyl alcohol: 90/10
Flow rate: 3 ml/min

EXAMPLE 6

Preparation of the Compound of Formula 13 (Process F)

20 mg (0.04 mmol) of the compound of formula 12 prepared in Example 5 was well mixed with 10 ml of acetone containing 5% water and 127 mg (0.9 mmol, 2.3 equivalent) of potassium carbonate at room temperature. 67 μl (0.6 mmol, 1.5 equivalent) of bromoacetateethylester was added thereto, followed by vigorous stirring for 4 hours. Upon completion of the reaction, the organic solvent was extracted by using sodium chloride solution and ethylacetate, which was dried over magnesium sulfate to eliminate moisture of the organic layer. After filtering, the solvent was distilled under reduced pressure, and the residue was purified by silica gel column chromatography (hexane/ethyl acetate=5/1, v/v) to give 22 mg (yield: 95%) of the target compound of formula 13.

$^1$H NMR (300 MHz, CDCl3): 7.98 (d, 2H, J=8.1 Hz), 7.65 (d, 2H, J=8.3 Hz), 7.06-7.27 (m, 7H), 6.55 (d, 1H, J=8.4 Hz), 4.59 (s, 2H), 4.53 (dd, 1H, J=9.7, 5.3 Hz), 4.22 (q, 2H, J=7.1 Hz), 3.37 (dd, 1H, J=13.7, 5.3 Hz), 3.17 (m, 1H) 2.20 (s, 3H), 1.83 (s, 3H), 1.26 (t, 3H, J=7.2 Hz) $^{13}$C NMR (75 MHz, CDCl$_3$): 169.1, 163.6, 156.9, 151.8, 138.3, 137.4, 137.3, 136.4, 133.4, 129.3, 128.9, 128.6, 127.2, 126.8, 126.3, 126.2, 126.1, 125.1, 111.8, 65.9, 61.7, 49.1, 44.4, 16.5, 15.1, 14.5

EXAMPLE 7

Preparation of the Compound of Formula 1 (Process G)

20 mg (0.03 mmol) of the compound of formula 13 prepared in Example 6 was mixed well with 15 ml of ethanol, to which 15 μl of 3 N sodium hydroxide solution was added. After stirring at room temperature for 20 minutes, pH of the reaction mixture was adjusted to 2.0 by 2 N HCl. Vacuum distillation was performed to eliminate ethanol about 80%. The organic solvent was extracted by using sodium chloride solution and ethyl acetate. After filtering, the solvent was distilled under reduced pressure, and the residue was purified by LH-20 column chromatography to give 16 mg (yield: 98%) of the target compound of formula 1.

$^1$H NMR (500 MHz, CDC13): δ 7.92 (d, 2H, J=8.2 Hz), 7.50 (s, 1H), 7.59 (d, 2H, J=8.2Hz), 7.07-7.22 (m, 6H), 6.85 (m, 1H), 6.44 (d, 1H, J=8.2 Hz), 4.47 (dd, 1H, J=9.7, 5.4 Hz), 3.39 (dd, 1H, J=13.8, 5.4 Hz), 3.06 (dd, 1H, J=13.8, 9.8 Hz), 2.12 (s, 3H), 1.73 (s, 3H) $^{13}$C NMR (125 MHz, CDCl$_3$): δ 164.1, 155.7, 151.2, 138.0, 137.9, 137.0, 136.4, 133.8, 131.8, 131.5, 129.0, 128.6, 127.2, 127.0, 126.6, 126.14, 126.11, 125.7, 125.0, 122.9, 122.7, 115.2, 60.8, 49.1, 43.7, 21.2, 15.9, 14.3, 14.2

EXPERIMENTAL EXAMPLE 1

Activity and Cytotoxicity Test

The PPARδ activities of the R-form compound represented by formula 1 of the present invention and the S-form compound represented by formula 2 were measured by transfection assay. In addition, the selectivity to PPAR subtypes, PPARα and PPARγ, was examined. Cytotoxicity was tested by MTT assay and in vivo activity and toxicity was investigated by animal experiment using mice.

[Transfection Assay]

CV-1 cells were used in this assay. The cells were inoculated in a 96-well plate containing DMEM supplemented with 10% FBS, DBS (delipidated) and 1% penicillin/streptomycin and cultured in a 37° C., 5% CO$_2$ incubator. The experiment was performed according to the steps of inoculation, transfection, sample treatment and confirmation. Particularly, CV-1 cells were inoculated in a 96 well-plate (5000 cells/well), followed by transfection 24 hours later. Full length PPARs plasmid DNA, reporter DNA confirming PPARs activity owing to its luciferase activity, β-galactosidase DNA providing information on transfection efficiency, and transfection reagent were used for the transfection. The compounds of formula 1 and formula 2 were dissolved in dimethylsulfoxide (DMSO), which were treated to the cells via media at different concentrations. After culturing the cells in the incubator for 24 hours, the cells were lysed by using lysis buffer. Luciferase activity and β-galactosidase activity were measured with Luminometer and a microplate reader. The obtained values of luciferase were modified by the values of β-galactosidase. A graph was made with those values and EC$_{50}$ was calculated.

TABLE 1

| compound | EC$_{50}$ (nM) | | |
|---|---|---|---|
| | PPARδ | PPARα | PPARγ |
| formula 1 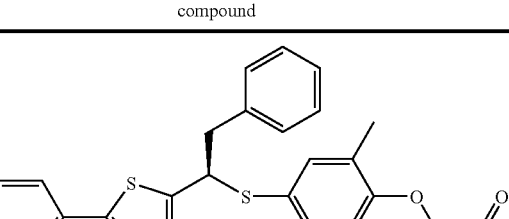 | 0.6 | ia | ia |
| formula 2 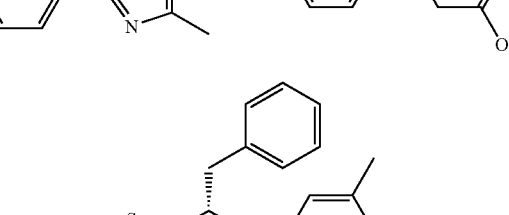 | 5.1 | ia | ia |

As shown in Table 1, the compound represented by formula 1 of the present invention is highly selective to PPARδ. The thiazole compound of formula 1 of the present invention demonstrated 100,000 times higher selectivity to PPARα and PPARγ. $EC_{50}$ of the compound of formula 1 to PPARδ was 0.6 nM and $EC_{50}$ of the compound of formula 2 to PPARδ was 5.1 nM. R-isomer, the compound of formula 1 of the present invention, exhibited 10 times stronger activity than S-isomer, the compound of formula 2. The above results indicate that the compound of formula 1 of the present invention has high selectivity.

[MTT Assay]

MTT assay was performed to test cytotoxicity of the compounds of the present invention. MTT is a yellow substance soluble in water, but when it is introduced into a living cell, it turns into a purple insoluble crystal by dehydrogenase in mitochondria. Cytotoxicity can be confirmed by measuring $OD_{550}$ after dissolving MTT in dimethylsulfoxide. The experiment was performed as follows.

CV-1 cells were inoculated in a 96-well plate (5000 cells/well). The cells were cultured in a 37° C. 5% $CO_2$ incubator for 24 hours, and treated with the compounds of formula 1 and formula 2 at different concentrations. Then, the cells were cultured for 24 hours again, to which MTT reagent was added. After culturing for 15 minutes, the generated purple crystals were dissolved in dimethylsulfoxide. Optical density was measured with a microplate reader to confirm cytotoxicity. As a result, the compound represented by formula 1 of the present invention and the compound represented by formula 2, the optical isomer thereof, were confirmed not to have cytotoxicity even at the concentration of 100,000 times the $EC_{50}$ value.

[Toxicity Test]

Acute toxicity and reproductive toxicity tests were performed using mice to evaluate the toxicity of the compound of the present invention. The compound of formula 1 was orally administered to ICR mice at 6 weeks at the dosage of 50 mg/kg, 300 mg/kg and 2000 mg/kg, followed by observation on toxicity for 14 days. As a result, no death was observed according to the administration of the compound of formula 1 even with the highest concentration of 2000 mg/kg, and no significant changes on weight and feed taking were observed either. Autopsy results showed no abnormal signs. The result of reproductive toxicity test using C57BL/6 mice was also consistent with the above, which is no toxicity caused by the compound of formula 1 was observed. After oral-administration of the compound to the pregnant female mice, weight gain and growth speed of fetus were investigated. As a result, no significant difference according to the administration was observed and no changes in bone development and disease related matters were observed.

[Animal Test]

[Obesity Inhibitory Effect]

An animal test using mice was performed to confirm the in vivo effect of the compound of the present invention. C57BL/6 (SLC Co.) mice at 14 weeks were used. To induce obesity, feeds containing 35% fat were given. While feeding such high-fat feeds for 35 days, vehicle, GW501516 (10 mg/Kg/day) and the compound of formula 1 of the present invention (10 mg/Kg/day) were orally administered. As a result, only 26.5% of the group treated with GW501516, 23.1% of the group treated with the compound of the present invention showed weight increase, compared with the vehicle treated group (58.9%), which was approximately ½ increase compared with the vehicle treated group. Therefore, the compound of formula 1 of the present invention was confirmed to have strong obesity inhibiting effect, which was much more excellent than GW501516.

[Diabetes Improving Effect]

GTT (glucose tolerance test) was performed to confirm the diabetes improving effect of the compound of the present invention. Glucose (1.5 g/Kg) was intra-abdominally administered to the mice pre-treated orally with samples for 78 days. Blood glucose was measured every hour. Fasting blood glucose was lower in the group treated with the compound of the present invention than in the group treated with vehicle or GW501516. The group treated with the compound of the present invention exhibited rapid blood glucose decrease in 20-40 minutes and glucose clearance in 100 minutes. In the meantime, the blood glucose level was not recovered to normal in the vehicle treated group even after 120 minutes. The GW501516 treated group showed lower blood glucose than the vehicle treated group but the blood glucose level was not recovered to normal. The above results indicate that the compound of formula 1 of the present invention had excellent diabetes improving effect.

[Hyperlipidemia Improving Effect]

In vivo animal test using C57BL/6 (SLC Co.) mice at 6 weeks was performed to confirm the hyperlipidemia improving effect of the compound of the present invention. The animals were orally administered with 10 mg/kg/day of the compound of formula 1 of the present invention and GW501516 while being fed with high fat feeds. 6 weeks later, blood was taken from orbital veins. Serum was separated and blood HDL level was measured by biochemical method. As a result, HDL level was 36.3% increased in the group treated with GW501516, compared with the control. HDL level was 44.6% increased in the group treated with the compound of formula 1 of the present invention. The above results indicate that the compound of formula 1 of the present invention increases blood HDL more effectively than GW501516.

[Arteriosclerosis Inhibiting Effect]

In vivo animal test using ApoE−/− mouse, which is an animal model for arteriosclerosis, was performed to confirm the arteriosclerosis inhibiting effect of the compound of the present invention. The animals were orally administered with 2 mg/kg/day of the compound of formula 1 of the present invention while feeding with high fat, high cholesterol feeds (20% fat, 1.25% cholesterol; AIN-93G diet). 28 days later, plaque staining was performed over the whole artery using Sudan IV to investigate the arteriosclerosis inhibiting effect of the compound by comparing the results between experimental and control groups. As a result, arteriosclerosis was 30% inhibited in ApoE−/− mouse treated with the compound of formula 1 of the present invention, compared with the control.

[Muscle Endurance Strengthening and Muscle Function Enhancing Effect]

An animal test was performed to confirm muscle endurance strengthening and muscle function enhancing effect of the compound of the present invention. Most muscles are generated in the developmental stage. Thus, the compound of formula 1 (10 mg/Kg/day) were orally administered to pregnant mice in the period of either pregnancy or lactation or both pregnancy and lactation. Weight gain and growth rate were not much different between fetuses of the control group and the treatment group. Muscles were observed after removing skin. As a result, muscles of the treatment group were red, unlike the controlled one. ATPase staining and immunostaining were performed. As a result, type I muscle fiber was increased in the group treated with the compound of formula 1. The effect of the changes of the muscle fiber on the enhancement of muscle endurance and muscle function was investigated by using treadmill test. As a result, running time was much extended in the group treated with the compound of formula 1.

TABLE 2

Results of muscle endurance test

| | Increasing rate (treatment group/control group) | | | | | |
|---|---|---|---|---|---|---|
| | pregnancy | | lactation | | Pregnancy + lactation | |
| | time | length | time | length | time | length |
| treatment group | 2.3 times | 2.4 times | 2.1 times | 2.2 times | 2.9 times | 3.0 times |

When the compound of the present invention was treated to adults, muscle endurance and muscle function were also enhanced. Particularly, the compound of formula 1 was orally administered to C57BL/6 mice at 10 weeks at the concentration of 10 mg/kg, during which the mice were forced to exercise. The exercise was performed with treadmill for 30 minutes once a day for 30 days, precisely at the speed of 2 meter/min for the first 5 minutes, at 5 meter/min for 5 minutes, at 8 meter/min for 5 minutes and at 20 meter/min for the last 5 minutes. At the finish, muscle endurance and muscle function enhancing effect was tested by using treadmill. As a result, the time (1.5 fold) and distance (1.6 fold) of exercise were all increased in the group treated with the compound of the present invention, when compared with the control.

[Memory Improvement]

An animal test was performed to investigate the therapeutic effect of the compound of the present invention on dementia and Parkinson's disease based on the memory improving effect thereof. To confirm the effect of the compound of the present invention in the period of brain development, the compound was orally administered to pregnant mice at the concentration of 10 mg/kg in the periods of pregnancy and lactation. Morris water maze test was performed to detect any changes of the brain functions of the treatment group and the control group. As a result, the average time spent to find the platform was much shorter in the group treated with the compound of formula 1, compared with the control group; precisely, the treatment group spent 6.8 sec to find the platform and the control group spent 24.2 sec at average, suggesting that the compound of formula 1 had an excellent memory improving effect.

The therapeutic effect of the compound of the present invention on dementia and Parkinson's disease based on the memory improving effect thereof was investigated using brain disease animal model (C57BL/6 mice at 10 weeks). First, LPS was injected into the mouse brain to construct brain disease animal model. The mice were divided into four groups according to the administration and exercise. The exercise was performed with treadmill at the speed of 2 meter/min for the first 5 minutes, at 5 meter/min for 5 minutes, at 8 meter/min for 5 minutes and at 20 meter/min for the last 5 minutes. At the finish, Morris water maze test was performed. The results are summarized in Table 3. As a result, the therapeutic effect of the compound of formula 1 of the present invention on dementia and Parkinson's disease via memory enhancement by the compound and exercise was confirmed in the brain disease animal model.

TABLE 3

Results of water maze test

| Experiment group | | Results of water maze test |
|---|---|---|
| control group | Exercise (X) | 36 seconds |
| | Exercise (O) | 29 seconds |
| treatment group | Exercise (X) | 25 seconds |
| | Exercise (O) | 13 seconds |

INDUSTRIAL APPLICABILITY

The thiazole derivative compound of the present invention as a PPARδ ligand, which has selective meanings from prior inventions, can be effectively used as a pharmaceutical composition for the treatment and prevention of arteriosclerosis or hyperlipidemia; for increasing high density lipoprotein (HDL); for the treatment and prevention of diabetes; for the treatment and prevention of obesity; for strengthening muscle or enhancing endurance; for improving memory; for the treatment and prevention of dementia or Parkinson's disease; and a composition for health food supplements, health beverages, food additives, functional cosmetics and animal feeds.

The invention claimed is:

1. A method for strengthening muscle or for enhancing endurance comprising administration of a therapeutically effective amount of a thiazole compound represented by Formula 1:

[Formula 1]

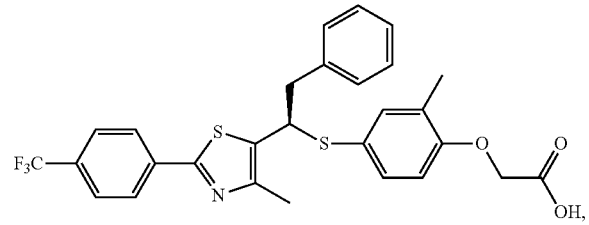

which is a peroxisome proliferator activated receptor δ (PPARδ) ligand,
or pharmaceutically acceptable salt thereof as an active ingredient.

* * * * *